United States Patent [19]

Nimry et al.

[11] 4,360,657

[45] Nov. 23, 1982

[54] TRICYCLO[6.4.0.0$^{2,7}$]-DODECANE-1,8,2,7-TETRACARBOXYLIC ACID DIANHYDRIDE AND POLYIMIDES THEREFROM

[75] Inventors: Tayseer S. Nimry, Wheaton; Ellis K. Fields, River Forest, both of Ill.

[73] Assignee: Standard Oil Company (Indiana), Chicago, Ill.

[21] Appl. No.: 294,322

[22] Filed: Aug. 19, 1981

[51] Int. Cl.$^3$ .............................................. C08G 73/10
[52] U.S. Cl. ...................................... 528/188; 528/125; 528/128; 528/189; 528/206; 528/208; 528/220; 528/229; 528/352; 528/353; 549/234
[58] Field of Search ............... 528/188, 189, 220, 352, 528/353, 229, 206, 208, 125, 128; 260/346.3

[56] References Cited

U.S. PATENT DOCUMENTS

| | | | |
|---|---|---|---|
| 3,468,825 | 9/1969 | Flowers et al. ..................... | 528/353 |
| 3,639,356 | 2/1972 | Bradshaw ........................... | 528/353 |
| 3,649,596 | 3/1972 | Smith, Jr. .......................... | 528/353 |
| 3,856,752 | 12/1974 | Bateman ............................ | 528/353 |
| 4,066,622 | 1/1978 | Feinstein et al. .................. | 528/353 |
| 4,142,036 | 2/1979 | Feinstein et al. .................. | 528/188 |
| 4,271,079 | 6/1981 | Maeda et al. ...................... | 528/353 |
| 4,271,288 | 6/1981 | Woo .................................... | 528/188 |

*Primary Examiner*—Lester L. Lee
*Attorney, Agent, or Firm*—Gunar J. Blumberg; William T. McClain; William H. Magidson

[57] ABSTRACT

Novel polyimides and molding compositions are prepared from tricyclo[6.4.0.0$^{2,7}$]dodecane-1,8,2,7-tetracarboxylic acid dianhydride. Also a novel dianhydride-,tricyclo[6.4.0.0$^{2,7}$]dodecane-1,8,2,7-tetracarboxylic acid dianhydride is prepared by a novel photodimerization of 1-cyclohexene-1,2-dicarboxylic anhydride. The polyimides are useful as engineering plastics.

52 Claims, No Drawings

TRICYCLO[6.4.0.0²,⁷]-DODECANE-1,8,2,7-TETRACARBOXYLIC ACID DIANHYDRIDE AND POLYIMIDES THEREFROM

BACKGROUND OF THE INVENTION

1. Field of the Invention

The field of this invention relates to the synthesis of, and to polyimides and copolyimides prepared from tricyclo[6.4.0.0²,⁷]-dodecane-1,8,2,7-tetracarboxylic acid dianhydride (I) or a mixture of this with other dianhydrides and diamines. These novel polyimides are useful in preparing molded articles, fibers, laminates and coatings. The field also includes novel dianhydrides useful in the manufacture of polyimides.

2. Background

It is known to make polyimides from pyromellitic dianhydride and aromatic diamines. This is disclosed in U.S. Pat. No. 3,179,634 (1965). British Patent Specification No. 570,858 discloses various processes for making fiber forming polymers.

In reviewing these references, it is clear that the use of I to form polyimides useful as moldings, fibers, laminates, and coatings has not been contemplated in the prior art. Neither has the art contemplated the novel dianhydride I prepared by photodimerization of 1-cyclohexene-1,2-dicarboxylic anhydride.

The general object of this invention is to provide novel polyimides and copolyimides based on I or I and another dianhydride and one or more diamine moieties. A more specific object of this invention is to provide polyimides from I and aliphatic, cycloaliphatic, araliphatic and aromatic diamines. Another object is to provide a new dianhydride I prepared by the photodimerization of 1-cyclohexene-1,2-dicarboxylic anhydride.

We have found that novel polyimides and copolyimides can be formed by reacting I and another dianhydride with diamines or mixtures of diamines. I reacts readily with the diamine to form a high molecular weight polyimide. In the novel process both aliphatic and aromatic diamines can be polymerized with I (or I in combination with another dianhydride) in the melt to form high molecular weight polyimides.

Our process for the manufacture of the novel polyimides and copolyimides comprises reacting about equal molar amounts of I with a primary diamine or a mixture of primary diamines. The molecular ratio of I to the primary diamine may be in the range of 1.2:1 to 1:1.2, preferably in the range of 1:1. In a suitable method, the reaction is conducted as a batch reaction at a temperature of about 130° C. to 300° C. for a period of about 2 to 8 hours in a nitrogen-containing organic polar solvent such as N-methyl-2-pyrrolidinone, N,N-dimethylacetamide or pyridine. I can be replaced partially by another aliphatic or aromatic dianhydride up to about 70 mole percent.

The other dianhydrides are characterized by the following formula:

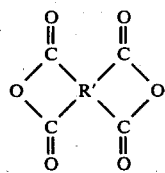

wherein R' is a tetravalent organic radical selected from the group consisting of aromatic, aliphatic, cycloaliphatic, heterocyclic, combination of aromatic and aliphatic, and substituted groups thereof. However, the preferred dianhydrides are those in which the R' groups have at least 6 carbon atoms wherein the 4 carbonyl groups of the dianhydride are each attached to separate carbon atoms and wherein each pair of carbonyl groups is directly attached to adjacent carbon atoms in the R' group to provide a 5-membered ring as follows:

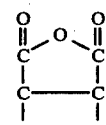

The preferred dianhydrides, as recited above, yield upon reaction with the diamines polyimides having outstanding physical properties. Illustrations of dianhydrides suitable for use in the present invention include: pyromellitic dianhydride; 2,3,6,7-naphthalene tetracarboxylic dianhydride; 3,3',4,4'-diphenyl tetracarboxylic dianhydride; 1,2,5,6-naphthalene tetracarboxylic dianhydride; 1,2,3,4-cyclopentane tetracarboxylic dianhydride; 2,2',3,3'-diphenyl tetracarboxylic dianhydride; 2,2-bis(3,4-dicarboxyphenyl)propane dianhydride; 3,4-dicarboxyphenyl sulfone dianhydride; 2,3,4,5-pyrrolidine tetracarboxylic dianhydride; 3,4,9,10-perylene tetracarboxylic dianhydride; bis(3,4-dicarboxyphenyl) ether dianhydride; 3,3',4,4'-benzophenonetetracarboxylic dianhydride; bis(3,4-dicarboxyphenyl)sulfide dianhydride; bis(3,4-dicarboxyphenyl)methane dianhydride; 1,4,5,8-naphthalenetetracarboxylic dianhydride; tricyclo [4,2,2,0²,⁵]-dec-7-ene-3,4,9,10-tetracarboxylic dianhydride; 3,6-etheneohexahydropyromellitic dianhydride; cyclobutane-1,2,3,4-tetracarboxylic dianhydride; and 1,3-dimethylcyclobutane-1,2,3,4-tetracarboxylic dianhydride. The polycondensation can also be carried out as a continuous process. The polycondensation can suitably be carried out at a temperature of 130° C. to 300° C. preferably at a temperature of 180° to 250° C. The novel polyimides of this invention have the following recurring structure wherein R is a divalent aliphatic or aromatic hydrocarbon radical:

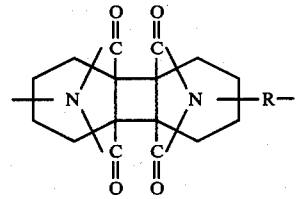

The radical R may be a divalent aliphatic hydrocarbon of 2 to 18 carbon atoms or an aromatic hydrocarbon from 6 to 20 carbon atoms, or an aromatic hydrocarbon radical containing from 6 to 10 carbon atoms joined directly or by stable linkage comprising —O—, methylene,

—SO—, —SO$_2$—, and —S— radicals. The radical R is derived from aliphatic, araliphatic or cycloaliphatic diamines such as ethylenediamine, propylenediamine, 2,2-dimethylpropylene diamine, tetramethylene diamine, hexamethylene diamine, octamethylene diamine, nonamethylene diamine, decamethylene diamine, dodecamethylene diamine, 4,4'-diaminodicyclohexylethane, xylylene diamine and bis (aminomethyl) cyclohexane. Suitable aromatic diamines useful in our process include para- and meta-phenylenediamine, 4,4'-oxydianiline, thiobis (aniline), sulfonylbis (aniline), diaminobenzophenone, methylenebis (aniline), benzidine, 1,5-diaminonaphthalene, oxybis (2-methylaniline), thiobis (2-methylaniline), and the like. Examples of other useful aromatic primary diamines are set out in U.S. Pat. No. 3,494,890 (1970) and U.S. Pat. No. 4,016,140 (1972) both incorporated herein by reference. The preferred diamines are hexamethylene diamine, dodecamethylene diamine and 4,4'-oxydianiline.

In some cases the polyimide may be further polymerized under "solid state polymerization" conditions. The term solid state polymerization refers to chain extension of polymer particles under conditions where the polymer particles retain their solid form and do not become a fluid mass. The solid state polymerization can be carried out below the melting point of the polyimide and can be conducted in several ways. However all techniques require heating the ground or pelletized polyimide below the melting point of the polyimide, generally at a temperature of about 175° to 300° C. while either sparging with an inert gas such as nitrogen or operating under vacuum. In cases where the polyimides and copolyimides have a low melt temperature, they can be polymerized in the melt under vacuum in thin sections or using thin film reactors known in the art.

Injection molding of the novel polyimide is accompanied by injecting the polyimide into a mold maintained at a temperature of about 25° C. to 150° C. In this process a 20 second to 1 minute cycle is used with a barrel temperature of about 125° C. to 350° C. The latter will vary depending on the T$_g$ of the polymer being molded.

The novel polyimides have excellent mechanical and thermal properties and can readily be molded into useful articles or formed into fibers, films, laminates or coatings.

Infrared spectra of the polyimides have confirmed the polyimide structure.

Analysis of the I-diamine polyimide by thermal gravimetric analysis shows excellent stability. Glass transition temperature T$_g$ of the polyimide varied with the particular diamine used. Values range from a T$_g$ of 60° C. to 140° C.

Diamines with the amino groups attached directly to the aromatic ring are suitably polymerized with I by solution condensation in organic polar solvents. These include N,N-dimethylacetamide, N-methyl-2-pyrrolidinone, N,N-dimethylformamide, pyridine, and the like. We have found that the polyimides and copolyimides of this invention are improved by the addition of reinforcing material. Suitably about 25 to 60 percent by weight of glass fibers, glass beads or graphite or a mixture of these can be incorporated into the polyimides and copolyimides. Any standard commercial grade then can be used as reinforcing agents. Glass beads ranging from 5 mm to 50 mm in diameter may also be used as reinforcing material. Injection molding of the novel glass-filled polyimide is accomplished by injecting the polyimide into a mold maintained at a temperature of about 50° to 150° C. In this process a 25 to 28 second cycle is used with a barrel temperature of about 125° to 350° C. The injection molding conditions are given in Table 1.

TABLE I

| Mold Temperature | 50 to 150° C. |
|---|---|
| Injection Pressure | 15,000 to 19,000 psi and held for 1 to 3 seconds |
| Back Pressure | 100 to 220 psi |
| Cycle Time | 25 to 28 seconds |
| Extruder: | |
| Nozzle Temperature | 125° C. to 350° C. |
| Barrels: | |
| Front heated to | 125° C. to 350° C. |
| Screw: | |
| 20 to 25 revolutions/minute | |

The following examples illustrate the preferred embodiment of the invention. It will be understood that the examples are for illustrative purposes only and to not purport to be wholly definitive with respect to conditions or scope of the invention.

EXAMPLE 1

Synthesis of Tricyclo[6.4.0.0$^{2,7}$]Dodecane-1,8,2,7-Tetracarboxylic Acid Dianhydride (I)

I is the photodimer of 1-cyclohexene-1,2-dicarboxylic anhydride (II), a monomer that is made by isomerizing the Diels-Alder adduct of butadiene and maleic anhydride, cis-4-cyclohexene-1,2-dicarboxylic anhydride with a few wt % of P$_2$O$_5$ [M. E. Bailey and E. D. Amstutz, JACS, 78, 3828 (1956)]. The photochemical reaction was carried out by dissolving 10.0 g of (II) and 1.0 g of benzophenone in 200 ml of acetone or chloroform. The solution was placed in a 250 ml pyrex flask that was equipped with a condenser and irradiated with light from a GE Sunlamp for 120 hours. The solution was roto-evaporated at 60° C. to ca. 40 ml, then allowed to cool in an ice bath. The white solid that precipitated was filtered and washed with a small volume of ice-cold acetone. Yield, 88%; mp, 276°-8° C. The product begins to decompose above 315° C. Analysis: Calcd. for C$_{16}$H$_{16}$O$_6$: C, 63.16; H, 5.25; MW, 304. Found: C, 63.14; H, 5.31; MW, 310. The $^{13}$C nuclear magnetic resonance spectrum is consistent with the formulation for I:

| C atom | $^{13}$C δ tms | C atom | $^{13}$C δ tms |
|---|---|---|---|
| a | 20.1 ppm | c | 51.1 ppm |
| b | 25.5 | d | 172.3 |

The above cited nuclear magnetic resonance spectrum data confirms the structure of I set forth hereinbelow:

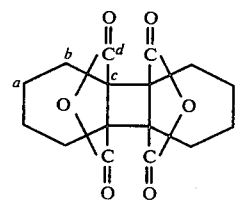

The mass spectral analysis is also in agreement with this formulation.

EXAMPLE 2

In a separate experiment conducted in an identical manner to Example 1, except that sunlight was used as a source of radiation instead of a GE Sunlamp, the yield reported above for I was accomplished after two weeks.

EXAMPLE 3

A three-neck, 100 ml flask containing a teflon-coated stirring bar was used. It was equipped with a nitrogen inlet, a glass stopper and a condenser, the end of which was fitted with a drying tube which also served as a nitrogen outlet. The reaction flask was flame-dried while being purged with nitrogen. Dodecamethylenediamine (DDA) 3.01 g (0.015 mole) was added and dissolved in 36 ml of N-methyl-2-pyrrolidinone (NMP) (dried over $P_2O_5$). To the resulting cloudy mixture 4.56 g (0.015 mole) of I was added all at once and the addition funnel was rinsed with 30 ml NMP. The mixture was stirred at 25° C. for one hour, at 100° C. for one hour and at 150° C. for one hour. At this point 10 ml of the solvent was removed by vacuum distillation. The temperature was increased to 250° C. and heating was continued for one and a half hours. The reaction mixture was cooled and mixed with water in a blender. The polymer was filtered, washed with water and dried in air for two hours, then in a vacuum oven at 150° C. for eight hours. The inherent viscosity (I.V.) for this polymer and all polymers in the following Examples was determined by dissolving 0.1 g of the polymer in 25 ml of a 60/40 mixture of phenol/tetrachloroethane at 130° C. then cooling to 30° C., the temperature at which I.V. was measured. I.V. for the polyimide of Example 3 was 1.48 dl/g. Analysis: Calcd. for $C_{28}H_{40}N_2O_4$=C, 71.8; H, 8.6; N, 6.0. Found: C, 71.5; H, 8.5; N, 5.7. A molded specimen had a Tg of 59° C. and a Tm of 169° C.

EXAMPLE 4

The same as Example 2 except that the total volume of NMP was 76 ml instead of 66 ml. The I.V. of the polyimide was found to be 0.68. Nitrogen analysis: Calcd: 6.0%. Found: 6.6%. A molded specimen had a Tg of 59° C. and a Tm of 182° C.

EXAMPLE 5

The procedure was the same as in Example 3. The diamine used was hexamethylene diamine (HMDA), 1.74 g (0.015 mole) and using 4.56 g (0.015 mole) of I. The total volume of NMP was 55 ml. The I.V. of the polyimide was 0.44. Nitrogen analysis: Calcd: 7.3%. Found: 7.1%. A molded specimen had a Tg of 137° C. and a Tm of 314° C.

EXAMPLE 6

To the reaction flask, 1.85 g (0.0159 mole) of HMDA was added and dissolved in 35 ml NMP. I, 5.0 g (0.0164 mole) and then added all at once. The addition funnel was rinsed with 20 ml of xylene mixture (dried over 4 Å molecular sieves). The mixture was heated at 80° C. for one hour and then at 200° C. for three hours. Approximately 20 ml of solvent containing most of the water by-product was removed. The polymer was mixed with water in a blender, filtered, washed again with water, dried in air for several hours, then in a vacuum oven at 100° C. for three hours. The I.V. of the polyimide was found to be 0.63. Nitrogen analysis: Calcd: 7.3%. Found: 7.6%.

EXAMPLE 7

A copolyimide was made by using an equimolar mixture of I and tetramethylcyclobutane tetracarboxylic dianhydride (III), the photodimer of dimethylmaleic anhydride. Thus, a flask containing a teflon-coated magnetic stirrer and equipped with a Dean-Stark trap, a nitrogen inlet, and a condenser, the end of which was fitted with a drying tube which served as a gas outlet was used. DDA (0.015 mole) was placed in the flask and dissolved in 20 ml NMP and 10 ml xylenes. To the solution a mixture of dianhydrides made up of 0.0075 mole of I and 0.0075 mole of III was added all at once. The addition funnel was rinsed into the flask with 20 ml NMP. After stirring at 25° C. for one hour the oil bath temperature was increased to 150° C. and held there for one hour to azeotrope the water by-product. The reaction temperature was increased again to 250° C. and heated for three hours. The polymer solution was then worked up as in Example 3.

The I.V. of the polymer was 0.42. Analysis: Calcd for $C_{52}H_{76}N_4O_8$: C, 70.6; H, 8.7; N, 6.3. Found: C, 70.4; H, 8.7; N, 6.2.

EXAMPLE 8

Using the procedure of Example 7 and 0.0075 mole of I, 0.0075 mole of III and 0.015 mole of HMDA, a new copolyimide was prepared. It had an I.V. of 0.40. Analysis: Calcd for $C_{40}H_{52}N_4O_8$: C, 67.0; H, 7.3; N, 7.8. Found: C, 66.4; H, 7.4; N, 7.9.

We claim:

1. A polyimide consisting essentially of the following recurring structure:

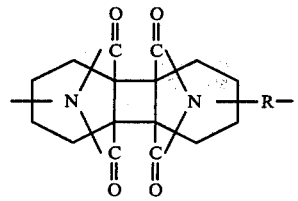

wherein R is a divalent aliphatic, cycloaliphatic, araliphatic or aromatic hydrocarbon radical.

2. The polyimide of claim 1 wherein R is an aliphatic hydrocarbon from 2 to 18 carbon atoms.

3. The polyimide of claim 1 wherein R is an aromatic hydrocarbon from 6 to 20 carbon atoms.

4. The polyimide of claim 1 wherein the aromatic hydrocarbon radical contains from 6 to 10 carbon atoms joined directly or by stable linkage selected from the group consisting of —O—, methylene,

—SO—, —SO$_2$— and —S— radicals.

5. The polyimide of claim 1 wherein the polyimide is in the form of a molded object.

6. The polyimide of claim 1 wherein the polyimide is in the form of a fiber.

7. The polyimide of claim 1 wherein the polyimide is in the form of a film.

8. The polyimide of claim 1 wherein the polyimide is in the form of a metal coating suitable for electrical service.

9. A polyimide consisting essentially of the following recurring structure:

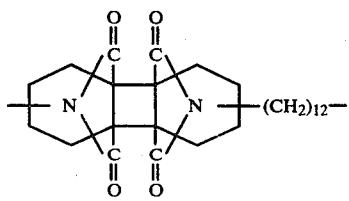

10. A polyimide of claim 9 wherein the polyimide is in the form of a molded object.

11. The polyimide of claim 9 wherein the polyimide is in the form of a fiber.

12. The polyimide of claim 9 wherein the polyimide is in the form of a film.

13. The polyimide consisting essentially of the following recurring structure:

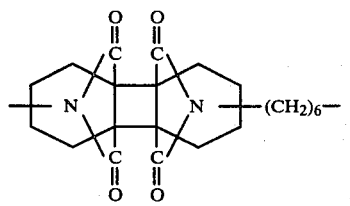

14. The polyimide of claim 13 wherein the polyimide is in the form of a molded object.

15. The polyimide of claim 13 wherein the polyimide is in the form of a fiber.

16. The polyimide of claim 13 wherein the polyimide is in the form of a film.

17. A polyimide consisting essentially of the following recurring structure:

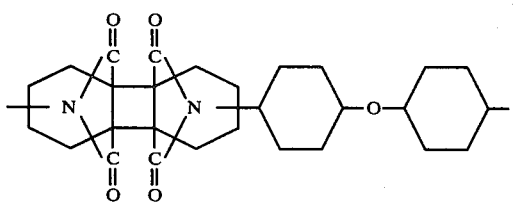

18. The polyimide of claim 17 wherein the polyimide is in the form of a molded object.

19. The polyimide of claim 17 wherein the polyimide is in the form of a fiber.

20. The polyimide of claim 17 wherein the polyimide is in the form of a film.

21. A copolyimide consisting essentially of the following structure:

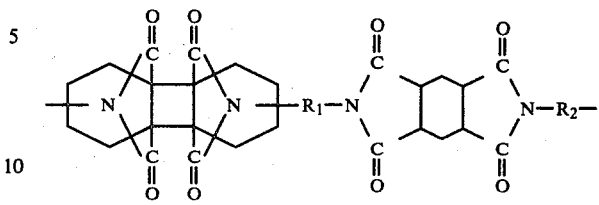

wherein $R_1$ and $R_2$ are the same or different divalent aliphatic, cycloaliphatic, araliphatic or aromatic hydrocarbon radicals.

22. The copolyimide of claim 21 wherein $R_1$ and $R_2$ are aliphatic hydrocarbons from 2 to 18 carbon atoms.

23. The copolyimide of claim 21 wherein $R_1$ and $R_2$ are aromatic hydrocarbons from 6 to 20 carbon atoms.

24. The copolyimide of claim 21 wherein the aromatic hydrocarbon radicals contains from 6 to 10 carbon atoms joined directly or by stable linkage selected from the group consisting of: —O—, methylene,

—SO—, —SO$_2$— and —S— radicals.

25. The copolyimide of claim 21 wherein the polyimide is in the form of a molded object.

26. The copolyimide of claim 21 wherein the polyimide is in the form of a fiber.

27. The copolyimide of claim 21 wherein the polyimide is in the form of a film.

28. The copolyimide of claim 21 wherein the polyimide is in the form of a metal coating suitable for electrical service.

29. A copolyimide consisting essentially of the following recurring structure:

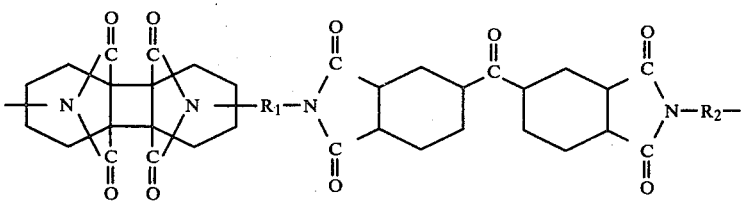

wherein $R_1$ and $R_2$ are the same or different divalent aliphatic, cycloaliphatic, araliphatic, or aromatic hydrocarbon radicals.

30. A copolyimide of claim 29 wherein the polyimide is in the form of a molded object.

31. The copolyimide of claim 29 wherein the polyimide is in the form of a fiber.

32. The polyimide of claim 29 wherein the polyimide is in the form of a film.

33. A copolyimide consisting essentially of the following recurring structure:

40. The copolyimide of claim 38 wherein X and X' are aromatic hydrocarbons of 6 to 20 carbon atoms.

41. A copolyimide consisting essentially of the following recurring structure:

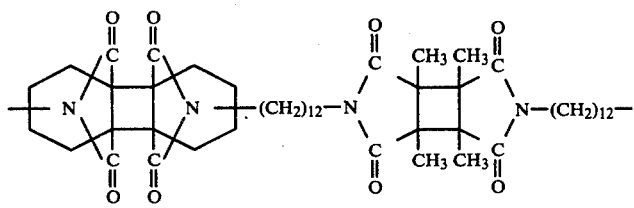

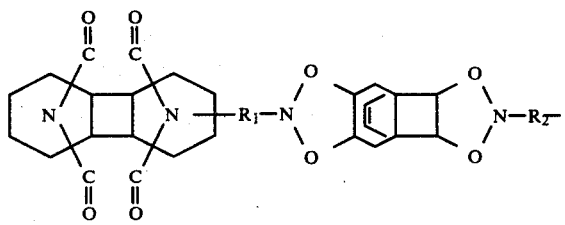

wherein R₁ and R₂ are the same or different divalent aliphatic, cycloaliphatic, araliphatic, or aromatic hydrocarbon radicals.

34. A polyimide of claim 33 wherein the polyimide is in the form of a molded object.

35. A polyimide of claim 33 wherein the polyimide is in the form of a fiber.

36. A polyimide of claim 33 wherein the polyimide is in the form of a film.

37. A copolyimide consisting essentially of the following recurring structure:

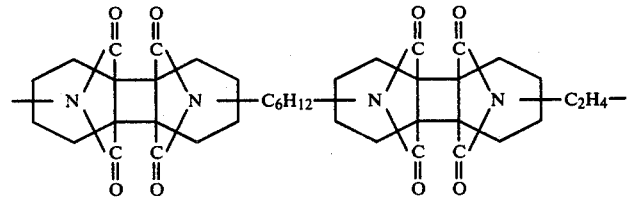

38. A copolyimide consisting essentially of the following structure:

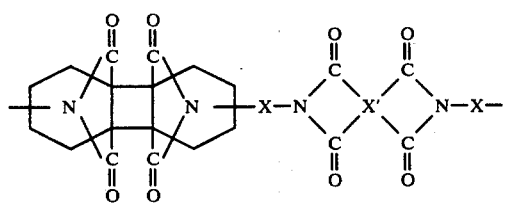

wherein X is a divalent hydrocarbon radical and X' is a tetravalent hydrocarbon radical.

39. The copolyimide of claim 38 wherein X and X' are aliphatic hydrocarbons from 2 to 18 carbon atoms.

42. A copolyimide of claim 41 wherein the copolyimide is in the form of a molded object.

43. A copolyimide of claim 41 wherein the copolyimide is in the form of a fiber.

44. A copolyimide of claim 41 wherein the copolyimide is in the form of a film.

45. A copolyimide consisting essentially of the following recurring structure:

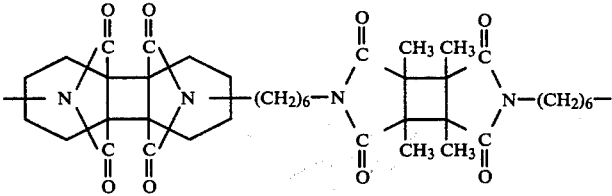

46. A copolyimide of claim 45 wherein the copolyimide is in the form of a molded object.

47. A copolyimide of claim 45 wherein the copolyimide is in the form of a fiber.

48. A copolyimide of claim 45 wherein the copolyimide is in the form of a film.

49. A copolyimide consisting essentially of the following recurring structure:

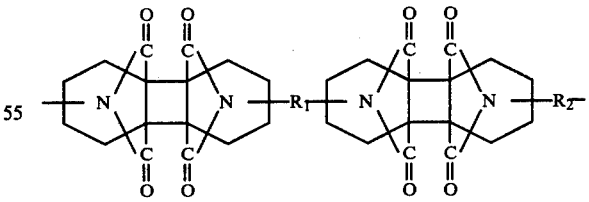

wherein R₁ and R₂ are different divalent aliphatic, cycloaliphatic, araliphatic or aromatic hydrocarbon radicals.

50. A copolyimide of claim 49 wherein the copolyimide is in the form of a molded object.

51. A copolyimide of claim 49 wherein the copolyimide is in the form of a fiber.

52. A copolyimide of claim 49 wherein the copolyimide is in the form of a film.

* * * * *

UNITED STATES PATENT AND TRADEMARK OFFICE
CERTIFICATE OF CORRECTION

PATENT NO. : 4,360,657
DATED : November 23, 1982
INVENTOR(S) : Tayseer S. Nimry, Ellis K. Fields It is certified that error appears in the above-identified patent and that said Letters Patent is hereby corrected as shown below:

Column 4, lines 21-22, "to not purport" should read -- do not purport --.

Column 5, line 58, "mole) and then" should read -- mole) was then --.

Signed and Sealed this

Fourth Day of October 1983

[SEAL]

Attest:

GERALD J. MOSSINGHOFF

Attesting Officer    Commissioner of Patents and Trademarks